United States Patent [19]

Nock et al.

[11] Patent Number: 5,776,066
[45] Date of Patent: Jul. 7, 1998

[54] METHOD AND APPARATUS FOR CREATING ADAPTIVELY FOCUSED ULTRASOUND IMAGES

[75] Inventors: Levin F. Nock; Barry H. Friemel, both of Issaquah, Wash.

[73] Assignee: Siemens Medical Systems, Inc., Iselin, N.J.

[21] Appl. No.: 723,170

[22] Filed: Sep. 30, 1996

[51] Int. Cl.⁶ .................................................. A61B 8/00
[52] U.S. Cl. ................................................................ 600/443
[58] Field of Search ...................... 128/660.07, 661.01, 128/660.06

[56] References Cited

U.S. PATENT DOCUMENTS 5,566,674 10/1996 Weng .................... 128/660.07

*Primary Examiner*—Francis Jaworski

[57] ABSTRACT

A method for creating ultrasound images determines if an ultrasound transducer is moving by more than a predetermined amount by obtaining two conventionally focused images $D_{K-1}$ and $D_K$. Each image is divided into a series of sections. An image processor searches the previous frame $D_{K-1}$ for data points found in the current frame $D_K$. Movement vectors are defined for each section that describe how the data points of a section move from the previous frame $D_{K-1}$ to the current frame $D_K$. The movement vectors are then applied to sections of a previously displayed adaptively focused frame $I_{K-1}$ in order to create a translated adaptively focused frame $I_{K-1'}$. A new adaptively focused frame is created by averaging the current adaptively focused frame $A_K$ with the translated frame $I_{K-1'}$.

10 Claims, 5 Drawing Sheets

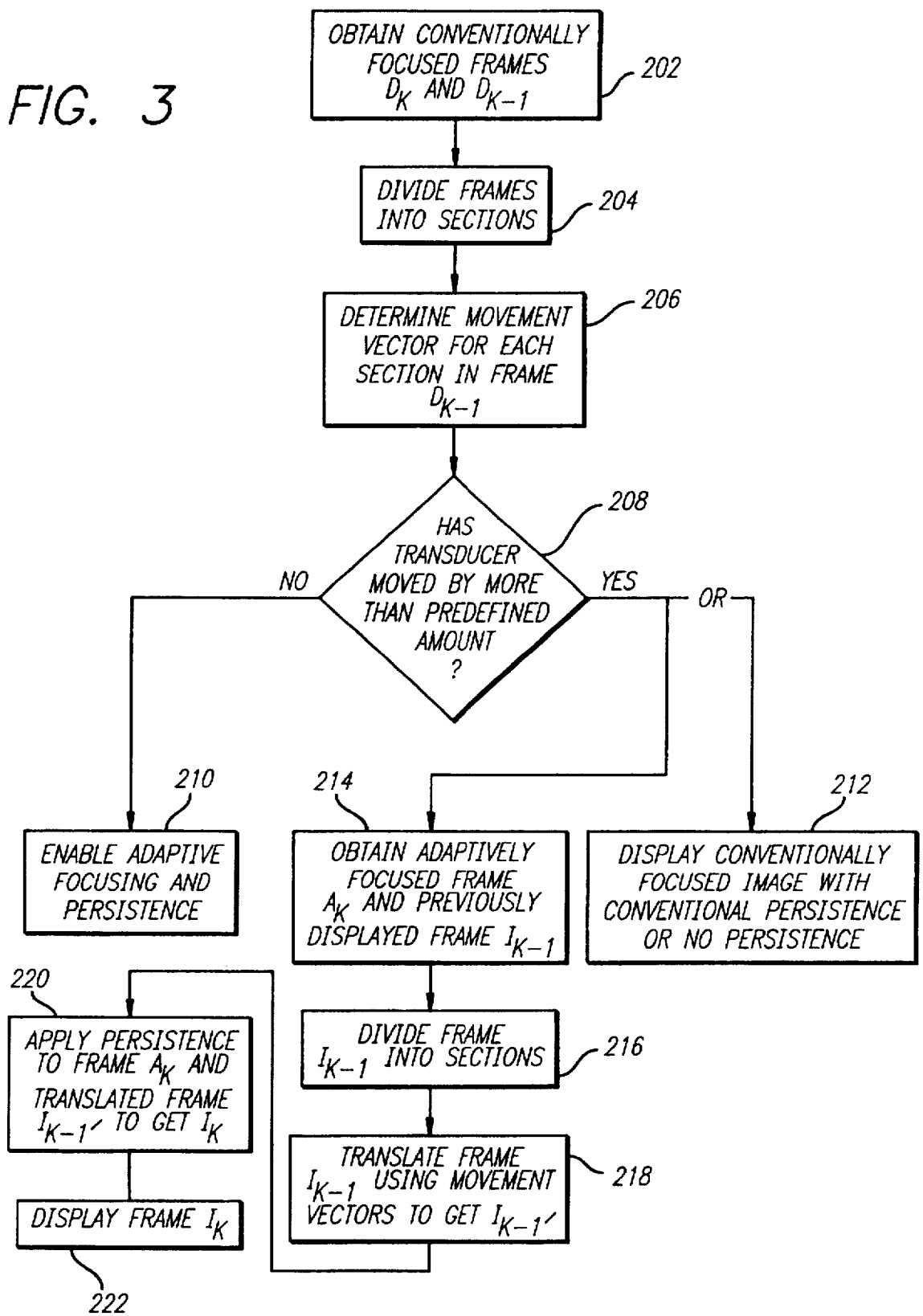

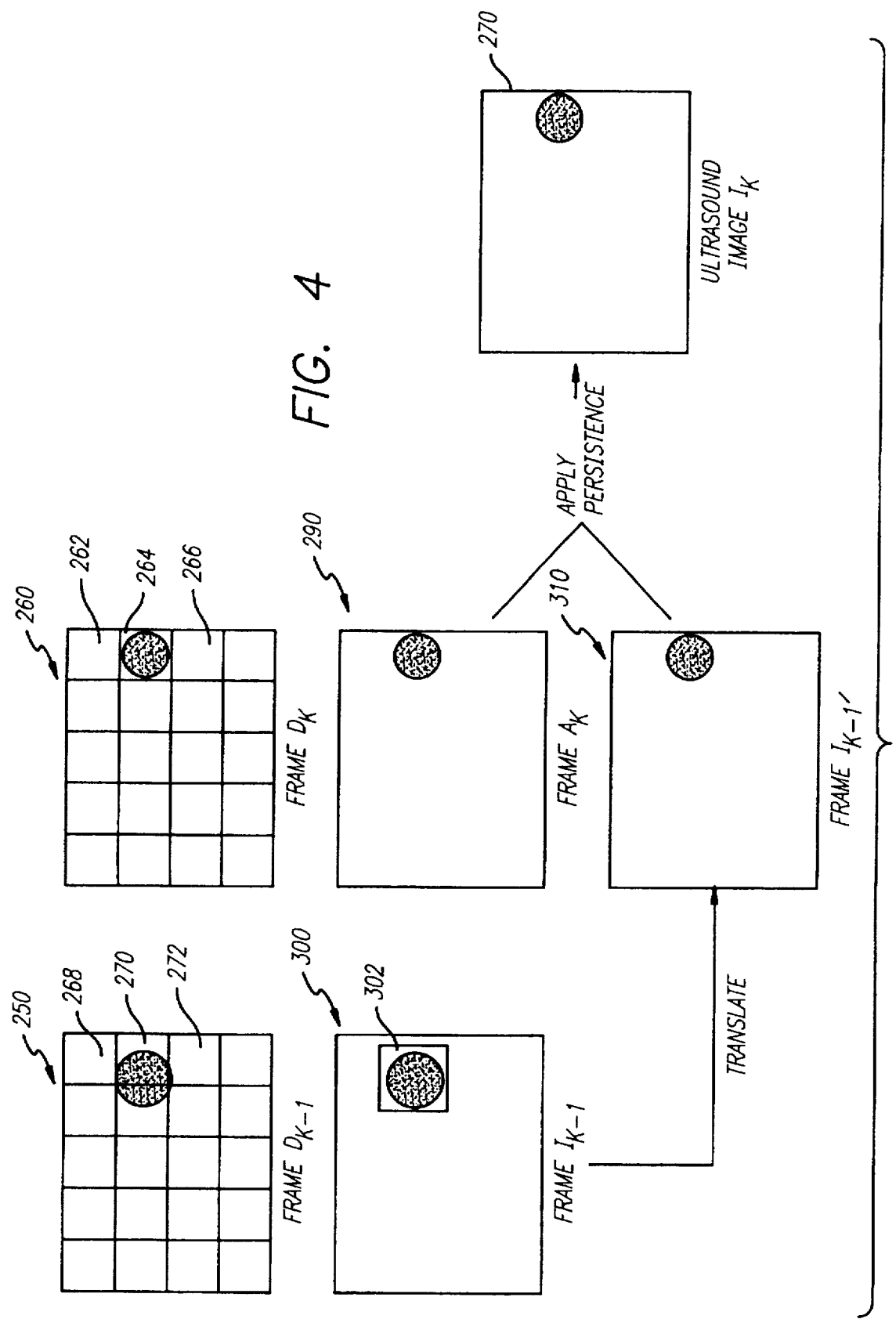

METHOD AND APPARATUS FOR CREATING ADAPTIVELY FOCUSED ULTRASOUND IMAGES

FIELD OF THE INVENTION

The present invention relates to ultrasound systems in general, and more particularly to methods of creating ultrasound images.

BACKGROUND OF THE INVENTION

Ultrasound systems provide a method of non-invasively imaging a patient's internal body matter by transmitting ultrasonic sound waves into the patient and detecting and analyzing the returned echoes. By determining the amplitude of the returned ultrasound echoes, a two-dimensional image can be created that shows the structure of the internal body matter.

The ability of the ultrasound system to produce a quality image of a particular point of interest in the patient's body is highly dependent upon the accuracy with which the echo signals received from the point of interest are focused. The time required for the echo signal to travel from the point of interest to an ultrasound transducer that receives the echo is a function of the speed of sound in the tissue through which the echo signal travels. The speed of sound is typically not constant in the body but varies with tissue type.

To improve the quality of an ultrasound image, adaptive focusing has been proposed whereby the focal delay for the echo signals produced by each element of the transducer is varied to compensate for the type of tissue found between the transducer element and the point of interest. While adaptive focusing can provide improved ultrasound images, it also causes the background noise or speckle pattern of the ultrasound image to flicker. This flicker is not only distracting for the physician or sonographer but causes eye fatigue that hampers the ability to diagnose the ultrasound image.

The conventional method of reducing image flicker in an ultrasound system is to use persistence. Persistence creates an image by averaging the data received for a new image with the data used to produce a previous image. While this technique works well if the transducer is held steady, the use of persistence creates a blurred or smeared image if the transducer is moved. The blurred image is even more distracting than the flickering images.

Therefore, given the shortcomings of prior art ultrasound imaging systems, there is a need for a method of stabilizing adaptively focused images without creating image blur.

SUMMARY OF THE INVENTION

To produce an ultrasound image having the benefits of adaptive focus without creating image blur, the present invention produces a persisted, adaptively focused ultrasound image. The ultrasound system first obtained two successive conventionally focused frames $D_{K-1}$ and $D_K$. Movement between the two frames is detected by dividing the frames into sections. A search for the displacement of the data points in each section of the current frame $D_K$ is conducted by performing a minimum sum, absolute difference search on the data points in each section of the previous frame $D_{K-1}$. The location in the previous frame having the minimum sum is defined to match the section in the current frame. Movement vectors are then defined for each section that describe the movement of the section between the previous frame $D_{K-1}$ and the current frame $D_K$.

To produce a new, adaptively focused image, an adaptively focused frames $A_K$ and a previously displayed frame $I_{K-1}$ are obtained. The previously displayed frame $I_{K-1}$ is divided into sections. Each section of the previously displayed frame $I_{K-1}$ is then translated according to a movement vector defined for a corresponding section of the previous conventionally focused frame $D_{K-1}$ in order to create a translated, adaptively focused frame $I_{K-1'}$. The ultrasound image is then created by averaging the data in the frame $A_K$ and the translated frame $I_{K-1'}$.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 3 is a flow chart showing the steps performed by the present invention to produce ultrasound images with reduced flicker; and FIG. 4 illustrates how an adaptively focused ultrasound frame can be translated in order to apply persistence according to the present invention.

DETAILED DESCRIPTION OF THE PREFERRED EMBODIMENT

As will be described in detail below, the present invention is a method of producing adaptively focused ultrasound images with reduced image blur or flicker.

Figure 1A:
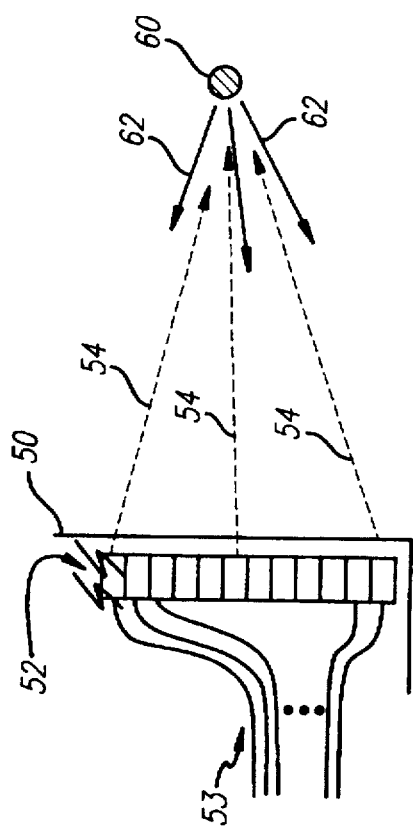
FIG. 1A is a simplified diagram of an ultrasonic transducer.

FIG. 1A illustrates the basic operation of an ultrasound imaging system. An ultrasound transducer 50 includes an array of transducer elements 52 that are made of a piezoelectric material. Each transducer element is connected to a pulse generator (not shown) via a separate lead 53. The pulse generator supplies electrical driving signals to the transducer elements 52, which the transducer elements convert into ultrasonic sound waves 54 that are directed into a patient's body. By controlling the timing and power of the driving signals, the ultrasonic sound waves 54 can be focused at a particular location in the patient's body.

A target 60 within the body reflects a portion of the ultrasonic sound waves as an echo signal 62 that is received by the transducer. The received echo signal causes the transducer elements to vibrate and produce a corresponding electrical signal. The electrical signal is fed to a receiver in the ultrasound system where it is digitized and analyzed to produce pixel data indicative of the strength of the echo. The pixel data is then used to create a corresponding ultrasound image so that a physician or sonographer can view the targets that create the echo signals.

The echo signals created as a result of the ultrasonic sound waves reflecting off various target elements do not reach each transducer element at the same time. The transducer elements that are located closest to the target element will receive the echo signal before those transducer elements that are located slightly farther from the target element. The ultrasound system compensates for the difference in distance by adjusting the time by which the electrical signals from each of the transducer elements are delayed before being summed together. The process of delay and summing is called beamforming and the time delays for the signals from all the transducer elements are called focal delays.

Figure 1C:
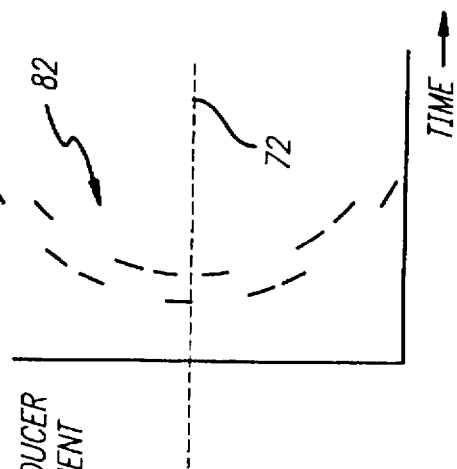
FIGS. 1B and 1C illustrate how adaptive focusing is used to provide an improved ultrasound image.
Figure 1B:
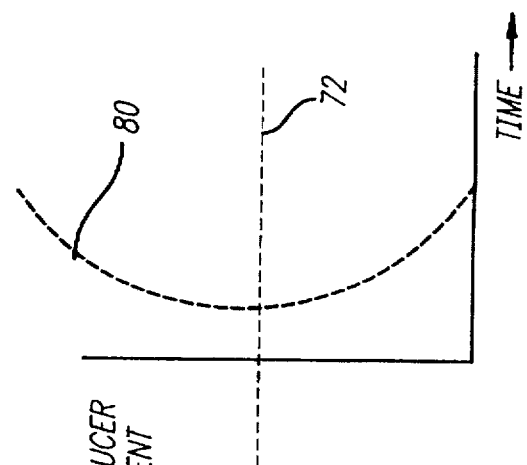

FIG. 1B illustrates a typical fixed set of focal delays or "delay profile" 80 that is used to focus echo signals received by the transducer. A typical ultrasound image is created by focusing the received echo signals along a series of receive beam lines 72. The electrical signals produced by the transducer elements located directly on the beam line are sampled first while those target elements located off the beam line are sampled later. The delay profile 80 therefore reflects the relative time at which the electrical signals produced by the transducer elements are sampled and combined. In conventional beamforming, the delay profile 80 is modified depending upon the location of the focal point of the echo signal on the beam line, according to techniques well known to those of ordinary skill in the ultrasound art.

As indicated above, the time at which the echo signals reach the transducer elements is highly dependent upon the type of tissue disposed between the transducer and the source of the echo. The tissue may not be homogeneous but may vary between one part of the transducer and another. For example, one portion of the transducer may be positioned over muscle while another portion of the transducer may be positioned over a layer of fat, etc.

To compensate for the differences in speed of sound characteristics for various tissue types, adaptive focusing techniques have been proposed whereby the focal delay at each transducer element is adaptively optimized to ensure the samples reflect the echo signals originating from the same location in the patient's body. Examples of adaptive focus techniques are described in U.S. Pat. Nos. 5,487,306; 5,423,318; 5,415,173; 5,331,964; 5,113,866, and International Applications Nos. PCT/US95/09929 and PCT/US95/09932.

FIG. 1C illustrates an adaptive focusing profile 82 used to sample the electrical signals produced by individual transducer elements. The profile 82 adjusts the focal delay at each transducer element as a function of the speed of sound between a transducer element and the desired focal point on the receive beam line 72.

The technique of adaptive focusing works well to improve the quality of an ultrasound image. However, the technique does have some side effects. One side effect is that the speckle pattern of an ultrasound image changes each time the adaptive focusing algorithm modifies the focal delay of a particular transducer element. The speckle pattern refers to the noise in the ultrasound image created by the coherent nature of ultrasound imaging when viewing subresolution target elements. The changing speckle pattern produces an image which appears to flicker on the screen and hampers the ability of the physician or sonographer to form diagnoses using the ultrasound image.

As indicated above, one common technique used to smooth an ultrasound image is to use persistence, whereby a new ultrasound image is created by averaging new echo signals with those used to create a previous image. With persistence, the data used to create the $K^{th}$ ultrasound image is defined by the equation:

$$I_K = D_K \alpha + (I_{K-1})(1-\alpha) \quad (1)$$

where: $D_K$ is the echo data received for the new image, and $I_{K-1}$ is the echo data used to produce the previous image. The weighting factor I can be static or dynamically adjusted either by the user of the ultrasound system or by the ultrasound system itself.

In another embodiment of persistence, the $K^{th}$ ultrasound frame, data $I_K$ is defined by:

$$I_K = \sum_{n=0}^{N} \alpha_n D_K - n \quad (2)$$

where $D_K - n$ is the data used to produce previous ultrasound images and where N is the order of a FIR filter. Still other examples of persistence are described in U.S. Pat. Nos. 4,887,306 and 5,503,153.

While persistence works to smooth successive ultrasound images if the transducer remains stable, the averaging process will cause the ultrasound image to smear if the transducer is moved. Furthermore, it is difficult to determine when an adaptively focused image is moving because the speckle pattern of the images is always changing whether the transducer is moving or not. Therefore, the present invention improves the quality of ultrasound images by determining if a transducer is moving and if so, by translating the previous adaptively focused image before applying persistence in order to prevent smearing.

Figure 2A:
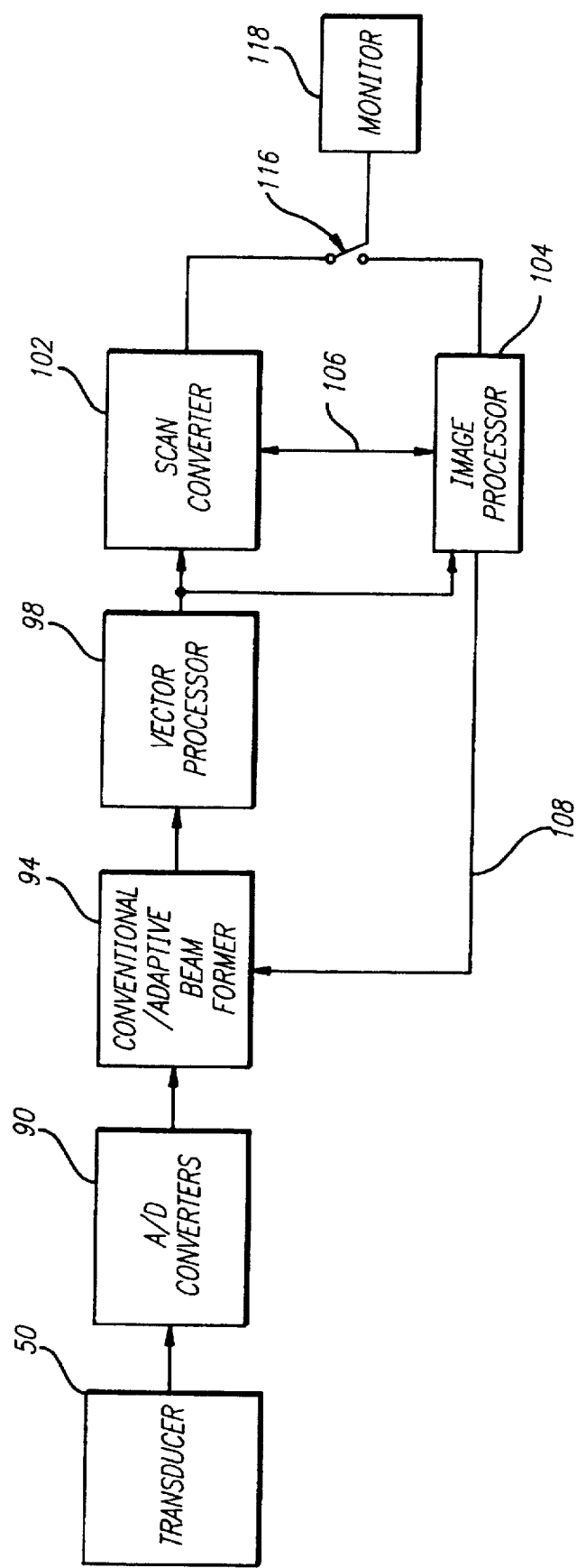
FIGS. 2A and 2B are block diagrams of two alternate embodiments of a receiver for use in an ultrasound system in which the present invention is implemented.

FIG. 2A is a block diagram of a first embodiment of a receiver of an ultrasound system that utilizes the method of the present invention. An ultrasound transducer 50 directs ultrasound signals into the patient and receives the echo signals in the manner described above. The electrical signals produced by the individual transducer elements are fed to analog-to-digital converters 90 that sample the electrical signals to produce digitized versions of the electrical echo signals. The output of the analog-to-digital converters 90 are fed to a beamformer 94 that is capable of conventional or adaptive beam forming. The beamformer adjusts the focal delay and the gain of the digitized echo signals. In addition, the beamformer 94 combines selected samples to produce a value representative of the echo amplitude at a particular position in the patient's body. The output of the beamformer is fed to an input of a vector processor 98 that filters the combined data produced by the beamformer.

The output of the vector processor 98 is echo data that is indicative of the echo magnitude at various positions along a series of beam lines. To convert this data to pixel data that can be used to create an ultrasound image, the output of the vector processor 98 is fed to an input of a scan converter 102. The scan converter 102 produces pixel data that is fed through a switch 116 to a monitor 118 in order to display an ultrasound image.

The ultrasound system also includes an image processor 104 having its own internal processor and memory. The image processor has an input that is coupled to the output of the vector processor 98 in order to receive the beam line echo data. In addition, the image processor is coupled to the scan converter 102 via a bi-directional data channel 106 in order to receive the pixel data produced by the scan converter. The image processor controls whether the beamformer 94 operates in a conventional focusing mode or in an adaptive focusing mode by transmitting control signals on a lead 108. Finally, the image processor controls the position of the switch 116 so that the monitor 118 is coupled either to the output of the scan converter 102 or to an output of the image processor.

As will be explained in detail below, the receiver shown in FIG. 2A operates by determining if the echo data indicates the transducer is moving. If so, then either the adaptive focusing is disabled and/or the persistence is reduced or the data received as a result of the adaptive focusing are compensated for the movement prior to applying persistence.

The persistence may be performed on the echo data either prior to, or after processing by the scan converter. To distinguish between the two modes, the data prior to scan conversion is called "frame data" while after scan conversion the data is called "image data."

Figure 2B:
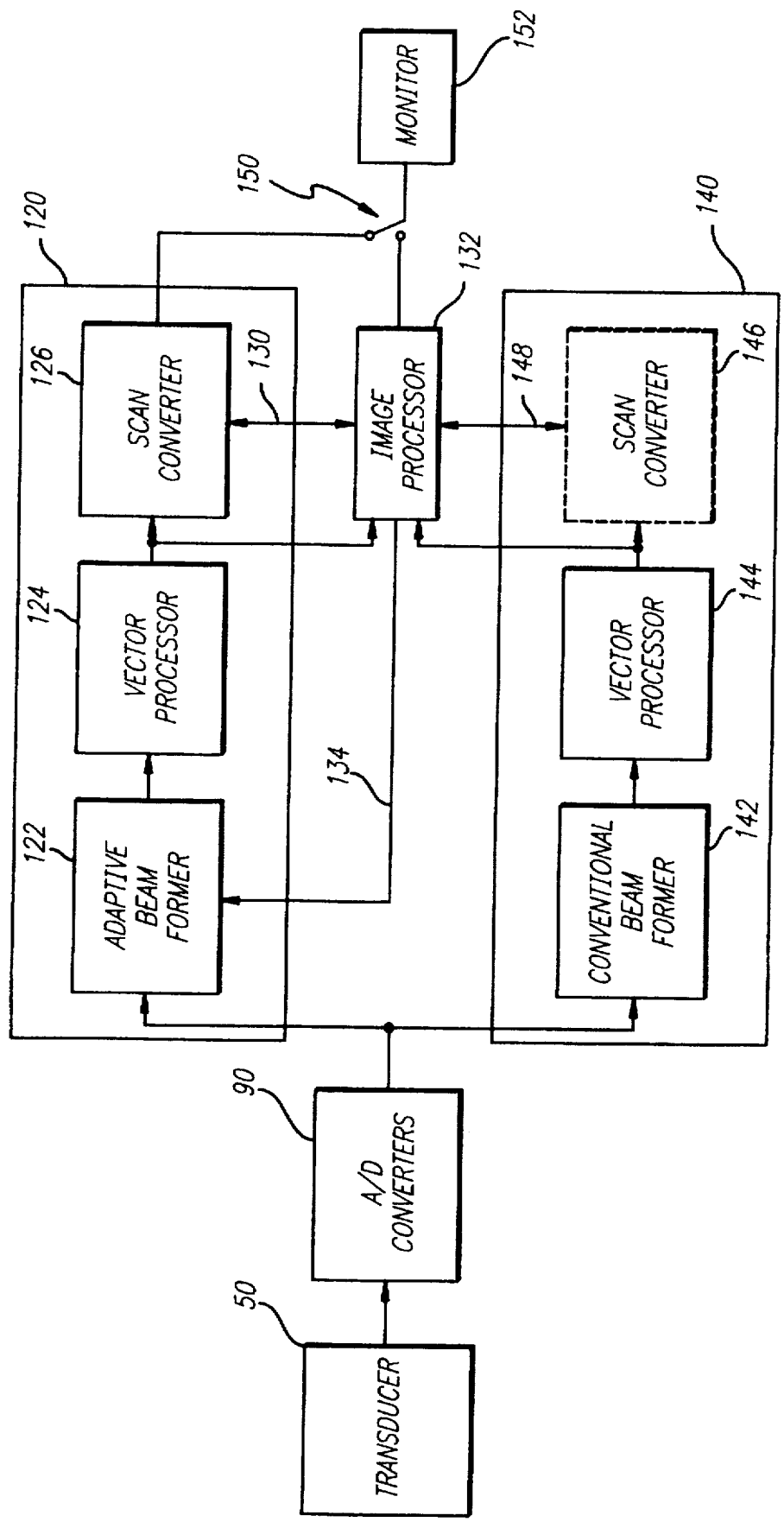

FIG. 2B shows an alternate embodiment of a receiver of an ultrasound system for implementing the present invention. Again, the ultrasound system includes a transducer 50 that transmits ultrasonic signals into the patient and produces electrical signals in response to received echo. The output of the transducer 50 is fed to a set of analog-to-digital converters 90 that operate in the same manner as described above. The digital signals produced by the analog-to-digital converters are fed into two channels 120 and 140. The first channel 120 creates adaptively focused ultrasound images while the second channel 140 creates conventionally focused ultrasound images.

The first channel 120 comprises an adaptive beamformer 122, a vector processor 124 and a scan converter 126. The digitized echo signals are applied to an input of the beamformer 122 that adjusts the focal delay and gain of the individual digitized echo signals and combines selected samples to create a single value representative of the echo amplitude at a particular position in the patient's body. The output of the beamformer is fed to an input of the vector processor 124 that filters the combined echo data. The output of the vector processor is fed to an input of the scan converter 126 that operates to translate the echo amplitude values into corresponding pixel values that are used to produce an ultrasound image.

The output of the scan converter 126 is applied to a switch 150 having two positions. In the first position, the switch 150 connects a monitor 152 to the output of the scan converter 126 to produce adaptively focused ultrasound images. In the second position, the ultrasound system produces conventionally focused ultrasound images as will be described below. The scan converter 126 is also coupled via a bi-directional data link 130 to an image processor 132 that includes a suitably programmed central processing unit or digital signal processor and memory in which the filtered frame data produced by the vector processor 124 or the image data produced by the scan converter 126 can be stored.

The digitized echo signals produced by the analog-to-digital converter 90 are also fed to the second channel 140 that comprises a conventional beamformer 142 and a vector processor 144. In addition the second channel may include its own scan converter 146. Each of these elements operates in the same manner as those described in connection with the first channel 120, with the exception that the focal delay times at which the beamformer 142 combines the samples of the individual digitized echo signals remain fixed from one frame to the next.

FIG. 3 is a flow chart indicating the steps taken by the ultrasound system to produce persistent, adaptively focused ultrasound images according to the method of the present invention. These steps are preferably implemented by the image processors 104 and 132 shown in FIG. 2A and 2B but could also be performed by a dedicated central processing unit or discrete components if desired.

Beginning with the step 202, the image processor obtains two successive conventionally focused frames $D_K$ and $D_{K-1}$. At step 204, the conventionally focused frames are divided into sections and at step 206, the image processor determines a series of movement vectors that define how the frame data or image data have moved from the previous frame $D_{K-1}$ to the current frame $D_K$.

FIG. 4 illustrates the method by which the movement vectors are determined. A frame 250 represents a previous, conventionally focused frame $D_{K-1}$, while a frame 260 represents the current, conventionally focused frame $D_K$. The frame 210 is divided into a series of sections 262, 264, 266, etc. (shown greatly enlarged for purposes of illustration). Each section preferably comprises approximately 8×8 data points. However, a greater or lesser number of data points could be used if desired.

The image processor analyzes each section in the current frame $D_K$ dividing the previous frame $D_{K-1}$ into a similar number of sections 268, 270, 272, etc. The image processor then expands each section of the previous frame in order to find the best match possible for the section in the current frame $D_K$. For example, the section 264 in the current frame is presumed to match the section 270 in the previous frame $D_{K-1}$. These sections will not exactly align however because the transducer may have moved. Therefore, the area of the section 270 is increased and a search is performed in the expanded area for the data points of the section 264 in the current frame $D_K$. The search is preferably performed using a minimum sum, absolute difference technique for computational simplicity. However, other techniques, such as least-squares, or routines using other metrics, could be used as available processing power allows.

With the minimum sum absolute difference technique, the difference between each of the data points in a section of the current frame is compared to a corresponding number of data points in the expanded area of the section in the previous frame. The values of the data points are subtracted and the absolute values of the differences between all the data points of the two sections is summed. The collection of data points that produces the minimum sum is determined to be the corresponding section of the previous frame.

Once the image processor has found the closest match between each section of the current frame and the previous frame $D_{K-1}$, a movement vector can be defined that describes the movement of the section. Each movement vector comprises a pair of values $\Delta X$ and $\Delta Y$ that indicate change in position of the section from the previous frame $D_{K-1}$ and the current frame $D_K$. This process continues for all the sections in the current frame $D_K$. The combination of the movement vectors for all of the sections in the previous frame defines how the overall image has changed from the previous frame to the current frame. If the transducer has moved between the two successive frames, then not every data point in the previous frame $D_{K-1}$ will be present in the current frame $D_K$.

Returning to FIG. 3, the image processor then determines whether the transducer has been moved by more than a predetermined amount at a step 208. The detection of movement is preferably determined by analyzing the movement vectors described above. For example, if any vector has a $\Delta X$ or $\Delta Y$ component (or a magnitude comprising the square root of the sum of the squares of the $\Delta X$ and $\Delta Y$ components) that is greater than some predefined constant, then the image processor determines that the transducer has moved by more than the predetermined amount. Although the presently preferred method of detecting transducer movement is accomplished by analyzing the movement vectors, movement of the ultrasound transducer could also be detected by a mechanical means as a motion sensor disposed within the transducer itself.

If the answer to step 208 is no, then the ultrasound system causes the monitor to display an adaptively focused image at a step 210. The pixel data for display is produced by averaging the data created in response to the new digitized echo signals with the data used to produce the previous adaptively focused frame—as is done with conventional persistence.

If the answer to step 208 is yes, and the transducer has moved by more than the predetermined amount, the present invention can be implemented in one of two modes. First, a single channel ultrasound system as shown in FIG. 2A, may disable the adaptive focusing in the beamformer. Conventionally focused images are then displayed using conventional persistence at a reduced level of persistence at step 212. In this case, the ultrasound system continues to display conventionally focused images until such time as the ultrasound system detects that the transducer is no longer moving.

An alternate and presently preferred implementation of creating ultrasound images when the transducer is moving involves applying persistence to the adaptively focused ultrasound images. To do this the ultrasound system obtains an adaptively focused frame $A_K$ and a previously displayed frame $I_{K-1}$ at step 214. At step 215, the ultrasound system divides the previously displayed frame $I_{K-1}$ into the same sections used to divide the previous conventionally focused frame $D_{K-1}$. At a step 218, the ultrasound system translates sections of the previous frame $I_{K-1}$ in accordance with the movement vectors determined between the conventionally focused frames $D_{K-1}$ and $D_K$ described above.

As shown in FIG. 4, a frame 290 represents the current adaptively focused frame $A_K$ and a frame 300 represents the previously displayed adaptively focused frame $I_{K-1}$. The previous frame $I_{K-1}$ is divided into sections such as section 302. These sections correspond in size and position to the sections defined for the previous conventionally focused frame $D_{K-1}$. The frame $I_{K-1}$ is then translated to a frame $I_{K-1'}$ by moving each of the sections in accordance with each of the movement vectors defined for the corresponding sections of the previous fixed frame $D_{K-1}$. The result of the translation is that the frame $I_{K-1'}$ is compensated for movement of the transducer. Not all the data points in the previous frame $I_{K-1}$ may appear in the subsequent frame $A_K$. Therefore, the translated frame $I_{K-1'}$ may be missing data points in some of its sections. The image processor must therefore keep a record of which sections contain data and which sections are empty. The difference between the sections containing data in the translated frame $I_{K-1'}$ and the current adaptively focused frame $A_K$ is a function of a change in the adaptive focusing algorithm. Therefore, the flicker that occurs as a result of the changing speckle patterns can be reduced by creating new adaptively focused ultrasound data $I_K$ that is a weighted average of the data points in current frame $A_K$ and the data in translated frame $I_{K-1'}$ according to the equation:

$$I_K = A_K \alpha + I_{K-1'}(1-\alpha) \quad (3)$$

This is shown as step 220 in FIG. 3. After the new frame $I_K$ is computed, it is displayed at step 222. Preferably, the weighting factor $\alpha$ is selected between 0 and 1 for the data points in the translated frame $I_{K-1'}$ that have non-zero values. For those sections the translated frame $I_{K-1'}$ that have zero values, the weighting factor is set to 1, so that the average frame simply mirrors the new data in the current frame $A_K$.

Although the method described above utilizes the frame data to create the persisted images, those skilled in the art will recognize that the same affect can be achieved by averaging the pixel data produced by the scan converters. In this case the movement vectors are determined by comparing the pixel data for two conventionally focused images $D_K$ and $D_{K-1}$. Movement vectors for the two images can then be determined. The movement vectors are then used to translate a previously displayed image $I_{K-1}$ which is averaged with the pixel data produced for a current adaptively focused image $A_K$.

If the method utilizes image data rather than frame data, the position of the switch 116 shown in FIG. 2A should be set so that the monitor receives the averaged pixel data produced at an output of the image processor 104. Similarly, the switch 150 shown in FIG. 2B should be set so that the monitor 153 receives the averaged pixel data produced at an output of the image processor 132. In addition, the scan converter 146 shown in FIG. 2B is required if conventionally focused image data are to be used in analyzing transducer movement.

The result of the present invention is that relatively flicker free, adaptively focused ultrasound images can be created even where the transducer is moved. The images are cleaner and are less blurred than previously adaptively focused images.

The embodiments of the invention in which an exclusive property or privilege is claimed are defined as follows:

1. A method of creating ultrasound images in an ultrasound system of the type that includes a transducer that transmits ultrasound signals into a patient and receives echo signals from the patient, comprising:
   obtaining a current set of conventionally focused echo signal data and a previous set of conventionally focused echo signal data;
   determining if the transducer has moved between the time when the current and the previous sets of conventionally focused echo signal data are obtained;
   obtaining a current set of adaptively focused echo signal data and a previous set of adaptively focused echo signal data,
   forming matched pairs of conventionally and adaptively focused echo signal data, the current set of adaptively focused echo signal data in each matched pair corresponding in time to the current set of conventionally focused echo signal data in the pair;
   translating the previous set of adaptively focused echo signal data to compensate for the transducer movement;
   averaging the current set of adaptively focused echo signal data and the translated set of adaptively focused echo signal data; and
   using the averaged set of adaptively focused echo signal data to produce an adaptively focused ultrasound image.

2. The method of claim 1, wherein the step of determining if the transducer has moved comprises:
   dividing the current and the previous sets of conventionally focused echo signal data into sections;
   determining a best matching position of each section of the current set of conventionally focused echo signal data in the previous set of conventionally focused echo signal data;
   defining one or more movement vectors that describe how sections in the previous set of conventionally focused echo signal data are moved to align with the current set of conventionally focused echo signal data; and
   analyzing the movement vectors to determine if the transducer has moved.

3. The method of claim 2, wherein the step of analyzing the movement vectors comprises:
   determining if the movement vectors have a magnitude that exceeds a predefined amount.

4. The method of claim 1, wherein the step of translating the previous set of adaptively focused echo signal data comprises:
   dividing the previous set of adaptively focused echo signal data into sections;
   moving each section of the previous set of adaptively focused echo signal data in accordance with the movement vectors defined for the previous set of conventionally focused echo signal data to create the translated set of adaptively focused echo signal data.

5. An ultrasound imaging system comprising:

an ultrasonic transducer that transmits ultrasonic signals into a patient and produces electrical signals upon the receipt of returned echo signals;

one or more analog-to-digital converters that receive the electrical signals produced by the ultrasonic transducer and convert the electrical signals to corresponding digital signals;

a first receiver channel coupled to receive the digital signals, the first receiver channel including a beamformer capable of producing adaptively focused echo signal data and a scan converter that receives the adaptively focused echo signal data and produces pixel data that is used to produce an adaptively focused image;

a second receiver channel coupled to receive the digital signals, the second receiver channel including a beamformer for producing conventionally focused echo signal data and a scan converter that receives the conventionally focused echo signal data and produces pixel data that is used to produce a conventionally focused image;

an image processor coupled to receive the adaptively focused echo signal data produced by the first receiver channel and the conventionally focused echo signal data produced by the second receiver channel, the image processor being programmed to determine whether the transducer is moving;

a display monitor selectively coupled to an output of the scan converter in the first or second receiver channel to display adaptively focused or conventionally focused ultrasound images; and a switch that couples the pixel data produced by the scan converter of the first or second receiver channel to the display monitor, the switch having a position that is controlled by the image processor.

6. A method of creating ultrasound images in an ultrasound system of the type that includes a transducer that transmits ultrasound signals into a patient and receives echo signals from the patient and a beamformer capable of producing conventionally focused or adaptively focused sets of echo signal data, comprising:

obtaining a current set of conventionally focused echo signal data and a previous set of conventionally focused echo signal data;

determining if the transducer has moved between the time when the current and the previous sets of conventionally focused echo signal data are obtained;

disabling the adaptive focus capability of the beamformer and creating sets of conventionally focused echo signal data.

7. A method of creating ultrasound images in an ultrasound system of the type that includes a transducer that transmits ultrasound signals into a patient and receives echo signals from the patient, comprising:

obtaining a current set of conventionally focused echo signal data and a previous set of conventionally focused echo signal data;

determining if the transducer has moved between the time when the current and the previous sets of conventionally focused echo signal data are obtained;

obtaining a current set of adaptively focused echo signal data and a previous set of adaptively focused echo signal data;

translating the previous set of adaptively focused echo signal data to compensate for the transducer movement;

averaging the current set of adaptively focused echo signal data and the translated set of adaptively focused echo signal data by scaling the current set of adaptively focused echo signal data by a value $\alpha$; by scaling the translated set of adaptively focused echo signal data by a value $1-\alpha$; and by adding the scaled data sets to produce the averaged set of adaptively focused echo signal data; and using the averaged set of adaptively focused echo signal data to produce an adaptively focused ultrasound image.

8. The method of claim 7, wherein some data points in the translated set of adaptively focused echo signal data may have a zero value, the method further comprising:

adjusting the value of $\alpha$ used to scale the data points in the translated set of adaptively focused echo signal data that have a zero value.

9. A method of creating ultrasound images in an ultrasound system of the type that includes a transducer that transmits ultrasound signals into a patient and receives echo signals from the patient, comprising:

generating beam line data in a beamformer;

obtaining a current set of conventionally focused echo signal data and a previous set of conventionally focused echo signal data, the beam line data forming the echo signal data;

determining if the transducer has moved between the time when the current and the previous sets of conventionally focused echo signal data are obtained;

obtaining a current set of adaptively focused echo signal data and a previous set of adaptively focused echo signal data;

translating the previous set of adaptively focused echo signal data to compensate for the transducer movement;

averaging the current set of adaptively focused echo signal data and the translated set of adaptively focused echo signal data; and using the averaged set of adaptively focused echo signal data to produce an adaptively focused ultrasound image.

10. A method of creating ultrasound images in an ultrasound system of the type that includes a transducer that transmits ultrasound signals into a patient and receives echo signals from the patient, comprising:

generating pixel data in a beamformer;

obtaining a current set of conventionally focused echo signal data and a previous set of conventionally focused echo signal data, the pixel data forming the echo signal data;

determining if the transducer has moved between the time when the current and the previous sets of conventionally focused echo signal data are obtained;

obtaining a current set of adaptively focused echo signal data and a previous set of adaptively focused echo signal data;

translating the previous set of adaptively focused echo signal data to compensate for the transducer movement;

averaging the current set of adaptively focused echo signal data and the translated set of adaptively focused echo signal data; and using the averaged set of adaptively focused echo signal data to produce an adaptively focused ultrasound image.

* * * * *